United States Patent
Wascher (10) Patent No.: US 7,311,714 B1
(45) Date of Patent: Dec. 25, 2007

(54) MARKING CATHETER FOR PLACEMENT USING FRAMELESS STEREOTAXY AND USE THEREOF

(76) Inventor: Thomas M. Wascher, 103 Pine Ct., Appleton, WI (US) 54914

( * ) Notice: Subject to any disclaimer, the term of this patent is extended or adjusted under 35 U.S.C. 154(b) by 135 days.

(21) Appl. No.: 10/791,112

(22) Filed: Mar. 2, 2004

(51) Int. Cl.
*A61B 19/00* (2006.01)

(52) U.S. Cl. .......................... 606/130; 606/1
(58) Field of Classification Search ........... 600/414, 600/417, 424, 429, 435, 421, 410, 433, 434; 604/116, 264; 606/129, 130, 1
See application file for complete search history.

(56) References Cited

U.S. PATENT DOCUMENTS

| | | | |
|---|---|---|---|
| 5,769,861 A | 6/1998 | Vilsmeier | |
| 5,787,886 A | 8/1998 | Kelly et al. | |
| 5,787,897 A * | 8/1998 | Kieturakis | 128/898 |
| 6,533,763 B1 * | 3/2003 | Schneiter | 604/264 |
| 6,613,002 B1 * | 9/2003 | Clark et al. | 600/593 |

OTHER PUBLICATIONS

Compass International, Inc., Jon S. Rousu, et al., Computer-Assisted Image Guided Surgery Using the Regulus™ Navigator, Jun. 25, 2000, Rochester, Minnesota, printed from www.compass.com on Jan. 8, 2004.
Lippincott Williams & Wilkins, Inc., Christopher Nimsky, et al., Quantification of, Visualization of, and Compensation for Brain Shift Using Intraoperative Magnetic Resonance Imaging, Neurosurgery, vol. 47, No. 5, pp. 1070-1080, Nov. 2000, Hagerstown, Maryland.
BrainLAB AG, Neurosurgery, 2000, Munich, Germany.
Compass International, Inc., Cygnus-PFS Product Information, Apr. 4, 2002, Rochester, Minnesota, printed from www.compass.com on Jan. 8, 2004.
Lippincott Williams & Wilkins, Inc., Gene H. Barnett, Intraoperative Magnetic Resonance Imaging, Contemporary Neurosurgery, vol. 24, No. 15, pp. 1-6, Jul. 31, 2002, Hagerstown, Maryland.
Frameless Stereotactic Surgery, printed from www.sd-neurosurgeon.com on Jan. 8, 2004.

* cited by examiner

*Primary Examiner*—Anhtuan T. Nguyen
*Assistant Examiner*—Melanie Tyson
(74) *Attorney, Agent, or Firm*—Reinhart Boerner Van Deuren s.c.

(57) ABSTRACT

A marking catheter made out of a flexible material and having a closed distal end and an open proximal end is provided. The marking catheter is sized and shaped to fit over the probe of a frameless stereotaxy system. One or more marking catheters may be positioned using the frameless stereotaxy system to define accurately an area identified in pre-operative imaging. For example, a plurality of marking catheters may be used to define physically the margins of a brain lesion. The brain lesion may then be removed to expose the positioned catheters, thereby assuring complete and effective lesion removal. The flexible catheters will move with any brain-shift occurring during lesion removal, thereby to maintain an accurate indication of the lesion margin.

14 Claims, 4 Drawing Sheets

MARKING CATHETER FOR PLACEMENT USING FRAMELESS STEREOTAXY AND USE THEREOF

FIELD OF THE INVENTION

The present invention pertains generally to surgical devices and appliances and, more particularly, to such devices as used in association with frameless stereotaxy and other systems used for performing surgery on the brain and other parts of the body, and methods for using such devices and appliances.

BACKGROUND OF THE INVENTION

Stereotaxy refers to a technique, most often applied to the nervous system, in which the contents of a patient's skull (or other portion of a patient's body) are considered in a precise three-dimensional space defined by a measuring instrument. Traditionally, the measuring instrument used to perform stereotaxy is a stereotactic frame, typically taking the form of a cage structure, that is fixed to the patient's skull or other part of the patient's body. Stereotactic frames are mechanical devices typically based upon a Cartesian or polar coordinate system. These systems typically include a means for securing the stereotactic frame device to the patient, at least one measuring scale for determining and confirming target coordinates and probe trajectories, and a probe holder or carrier.

The probe holder or carrier is used to direct a surgical probe or some other instrument to a desired three-dimensional location within the work space that is defined with respect to the geometry of the stereotactic frame. In a typical application, the stereotactic frame is used to position a probe or other instrument inside the body into an anatomic or pathological structure. The frame coordinates for the target structure are determined from stereotactic imaging studies performed using computed tomography (CT), magnetic resonance imaging (MRI), ultrasonography, etc. For CT and MRI based stereotaxis, the coordinates for an intra-cranial target are derived from stereotactic CT and MRI imaging examinations that are performed with the patient's head fixed in the rigid, confining, stereotactic frame. CT and MRI opaque external fiducial reference marker systems are applied to the frame to facilitate and simplify the calculation of stereotactic coordinates from the imaging.

Computer based interactive stereotactic methods allow tumors identified by CT and MRI to be considered as volumes in space and provide a surgeon with graphical displays that indicate the CT and MRI defined boundaries of the lesion within a defined stereotactic surgical field. In these procedures a tumor volume is reconstructed from stereotactic CT or MRI data and reformatted along a surgical viewing trajectory defined by a stereotactic frame. During surgery, an operating room computer system displays cross sections of the reformatted tumor volume with respect to surgical instruments directed into the surgical field using the stereotactic frame as a reference source. Intra-operatively, the surgeon monitors the computer-generated image of the surgical field which was derived from CT or MRI scans, as well as the surgical field itself. Systems have been developed for the super-imposition of the computer image upon the surgical field by means of a heads-up display unit attached to an operating microscope. This allows the surgeon simultaneously to view updated reformatted and scaled images of the CT or MRI defined surgical field visually superimposed upon the actual surgical field.

Stereotactic systems using stereotactic frames have a series of limitations. Stereotactic frames are cumbersome in general. They are especially cumbersome for procedures requiring more than a few target points and in volumetric stereotactic procedures where the demands of the procedure dictate the need for a larger working area, yet where such demands come into conflict with the physical structure of the frame. A conventional stereotactic frame is typically a cage structure extending about the patient's head that inherently restricts freedom of movement of the surgeon. Changing a target point or trajectory to reach a target point involves a mechanical adjustment of the stereotactic frame. Many such mechanical adjustments become very cumbersome when a surgeon is confronted with an infinite number of points from which to define a boundary of a volumetric lesion. In addition, the stereotactic reference frame must be applied to the patient's head in order to acquire pre-operative images. Some surgeons find the stereotactic frame application procedure difficult and time consuming. Patients also find this uncomfortable. In addition, the necessity to repeat CT and MRI examinations with the frame attached for obtaining pre-operative images increases the cost to patients.

In order to overcome the limitations associated with using stereotactic frames, various "frameless" stereotaxy systems have been developed. Frameless stereotaxy systems enable stereotactic guided surgery with a minimal structure present, thereby minimizing interference with the surgical procedure while providing enhanced accuracy in stereotactic imaging assistance to the surgeon. In a frameless stereotaxy system a probe or other medical instrument or device in the hand of a surgeon is tracked in three-dimensional space using an optical, electromagnetic, or other tracking system that interferes only minimally with the surgeon's use of the instrument. Pre-operative MRI or CT images are registered to the surgical field by indicating, with the stereotaxy system probe, locations on the patient's body or otherwise within the surgical field that correspond to points in the pre-operative images. For example, markers may be placed on a patient's anatomy (e.g., on the scalp or skull) while the pre-operative MRI or CT images are obtained. The stereotaxy system probe is then used to indicate the same marker positions in the real three-dimensional space under observation of the stereotaxy system after the patient has been positioned for surgery. Once the frameless stereotaxy system is registered in this manner, the surgeon may use a graphical display of the pre-operative images (e.g., rendered into a three-dimensional graphical representation) as registered to the surgical field, as provided by the system, accurately to position the probe, or other instrument, whose position is being tracked by the system, into a desired position in the patient's body. The frameless stereotaxy system display shows the tracked position of the probe or other instrument in real space relative to the registered pre-operative imagery Brain-shift is a major limitation of all neuro-navigational systems that rely on pre-operative imaging data. With ongoing surgery a remarkable deformation of the brain tissue may occur, resulting in navigational localizing errors as the real position of brain structures varies from that indicated in the pre-operative imaging. Brain-shift, also known as post imaging brain distortion or brain deformation, summarizes the behavior of brain tissue during surgical manipulations, i.e., opening of the cranium and dura, resection of tissue, use of brain retractors, and loss of cerebral spinal fluid. Negative or positive brain-shift, corresponding to infalling of the brain or swelling or expansion of compressed normal brain tissue because of tumor debulking, may occur. Experienced neurosurgeons can use various techniques to minimize the effects of brain-shift during the surgical procedure.

The shifting of cortical structures must be taken into account when superficial tumors adjacent to eloquent cortical brain areas, such as the motor area or speech related areas, are removed. This shifting often does not concern neurosurgeons, because in most cases the shifting is clearly visible during the surgical procedure and therefore can be easily compensated for. However, shifting of deep structures, so-called subsurface shifting, is much more relevant. Shifts of a deep tumor margin can lead to incomplete or too-deep resection. Subsurface deformation must be taken into account when neuro-navigation systems, which cannot be trusted for evaluation of deep tumor margins once surgery has begun, are used.

As tumor resection proceeds, brain-shift may result in significant inaccuracy of the navigation system for a high percentage of patients, so that as the operation proceeds some correction of the navigation system must be performed if it is to be relied upon. Intra-operative imaging using MRI provides the possibility of updating the navigation system with real data on the deformed brain. Intra-operative updating depends on the availability of an intra-operative MRI system. It is not only cost intensive but also time consuming. Intra-operative ultrasonography may be a choice for real-time updating of neural-navigation systems in the future. Ultrasonagraphic data could, for example, be used automatically to deform a preoperative MRI scan to match the shifted brain.

Different mathematical models that attempt to describe the brain-shift phenomenon have been developed in recent years. Some try to compensate for the brain-shift by using an intra-operatively guided deformable model that is based on the modeling of brain tissue as a homogenous linear viscoelastic material. Finite-element models describing the deformation of brain tissue are under investigation. However, there are inter-individual differences in brain-shift behavior, and brain tissue properties might change during surgical procedures, because of changes in intra-cranial pressure or blood carbon-dioxide concentrations or because of alterations of the water content of the brain after the administration of osmotically active drugs.

Attempts have also been made to modify preoperative imaging data, so that the images match the real intra-operative deformed brain, by measuring only several points during the surgical procedure, e.g., using optical scanning of the brain surface or ultrasonography. These limited intra-operative data are called sparse data.

A much more simple method that has evolved for mitigating the problems associated with brain-shift during tumor removal involves placing flexible catheters or pledgets around the tumor boundary using stereotactic frame navigation early in the procedure, before resection. The catheters provide visible limits to the resection that will track any shift or deformation that occurs. Thus, intra-operative re-imaging is not required.

What is desired is an improved system and method for using frameless stereotaxy to mark the margins of a brain lesion or other internal structure such that the ability of a neurosurgeon completely to remove a tumor while minimizing the removal of surrounding normal tissue is improved despite brain-shift that may occur during the resection process.

SUMMARY OF THE INVENTION

The present invention allows a neurosurgeon more accurately and completely to remove a brain lesion while minimizing the likelihood that healthy surrounding brain tissue will be damaged by the procedure. The present invention allows a neurosurgeon to take full advantage of pre-operative brain imaging, obtained using computed tomography (CT) or magnetic resonance imaging (MRI) scans, in combination with frameless stereotaxy accurately to define the boundaries of the lesion such that the lesion accurately can be resected during the surgical procedure. In accordance with the present invention, the lesion margins are defined in a manner such that brain-shift that may occur during the resection does not affect the ability of the surgeon accurately and completely to remove the tumor. In accordance with the present invention, one or more thin and flexible catheters are placed into the brain, using a frameless stereotaxy system for guidance before the resection has begun, to define the margins of the lesion to be resected. The catheters are designed to fit over a frameless stereotaxy system localizing probe and, using a frameless stereotactic localization procedure, are placed in positions to define the margins of the lesion in question. The resection then proceeds as normal, e.g., using ultrasonic resection, until the catheters are exposed at all margins of the resection cavity. In this fashion the surgeon is assured that all of the lesion is resected. The catheters will move with the surrounding brain as the brain shifts during the course of the resection, negating the affect of intra-operative brain-shift. The localizing catheters are removed after the resection is completed.

The present invention makes use of conventional frameless stereotaxy systems and methods. A conventional preoperative imaging system, e.g., a CT, MRI, or ultrasound scanning system, is used to obtain images of the patient's brain or other area of interest, e.g., to determine the extent of a lesion in the brain. Surface markers may be placed on the patient's external anatomy (e.g., scalp or skull) during the pre-operative imaging procedure such that the markers appear on the pre-operative images obtained. These markers will remain on the patient during the resection procedure. The pre-operative images thus obtained are provided to a frameless stereotaxy system computer.

A conventional frameless stereotaxy system includes a probe or other medical instrument as well as a position detection system for determining the position of the tip of the probe or other instrument in the three-dimensional surgical space. For example, optical or electromagnetic systems are known for tracking the probe location in the surgical field and providing that location to the stereotaxy system computer. After the patient is placed in position for surgery, the surgeon may use the probe and position detection system to indicate to the stereotaxy system computer the positions in real space of the markers placed on the patient's anatomy. This information is employed by the system computer to register the pre-operative images obtained with the actual surgical field. The tracked probe position and pre-operative imaging may then be combined to provide a computer generated image of the probe location relative to the registered pre-operative images as the surgeon moves the probe through the surgical field.

After preparing the surgical site, e.g., to expose the area of the brain upon which surgery is to take place, the surgeon mounts a marking catheter in accordance with the present invention onto the frameless stereotaxy system probe. In accordance with the present invention, the marking catheter preferably is made of a thin soft or flexible material, such as silicone rubber (e.g., Silastic). The marking catheter is sized to fit over the frameless stereotaxy system localizing probe with a closed end of the catheter at the distal end of the probe. A flange may be provided at the opposite open end of the catheter to aid in manually sliding the catheter off the probe once it is in position. The external surface of the catheter preferably may be marked with length indicators, e.g., rings and/or dots, to assist the surgeon in visualizing the depth of the target lesion. The catheter preferably may be made of a brightly colored material to enhance visualization thereof during the operative procedure.

Using the image guidance provided by the frameless stereotaxy system, the surgeon uses the system probe to position one or more catheters in accordance with the present invention in the patient's brain in and/or around a lesion identified in the pre-operative imaging. For example, the surgeon may use the probe to position marking catheters in accordance with the present invention along the anterior, posterior, superior, inferior, etc. margins of the lesion in question. The marking catheters preferably are advanced to the appropriate depth within the brain along the lesion margins such that the closed distal ends of the catheters, when placed into position, correspond to the tumor depth margin. Each catheter may be cut off at the surface of the brain after it is placed in position and the frameless stereotaxy system probe is removed therefrom.

Having positioned one or more marking catheters in accordance with the present invention into the brain to define the margins of the lesion to be resected, the resection of the lesion may proceed in a normal manner, e.g., using conventional micro-surgical techniques. Tumor removal continues until the marking catheters that define the margins of the lesion have been exposed down to their tips. Since the marking catheters are soft and pliable, they will move as the surrounding brain shifts into the cavity of tumor resection, maintaining their positions at the lesion margins, thereby virtually eliminating the error associated with brain-shift. Once all of the catheters have been exposed by way of tumor resection, the surgeon is assured that gross total tumor removal has been accomplished with minimal damage to surrounding normal tissue. At this point the marking catheters can be removed, and the procedure completed in the normal manner.

The present invention thus provides for the use of a frameless stereotaxy system to enhance surgical accuracy in a manner that compensates for brain-shift without requiring, e.g., expensive and complicated intra-operative re-imaging. The present invention may be applicable not only to the removal of brain lesions, but also to the removal of tumors in other areas of the body and/or other surgical procedures.

Further objects, features, and advantages of the invention will be apparent from the following detailed description taken in conjunction with the accompanying drawings.

DETAILED DESCRIPTION OF THE INVENTION

The present invention provides for the improved use of frameless stereotaxy systems to improve surgical results. The present invention will be described in detail herein with reference to use thereof for the accurate and complete resection of brain lesions. In this application, the present invention employs a frameless stereotaxy or neuro-navigation system to define accurately the margins of the lesion to be resected in a manner such that the error typically associated with brain-shift occurring during lesion removal is eliminated without requiring expensive and complicated intra-operative imaging. In this way complete tumor removal can be assured with minimized impact on surrounding normal tissue. It should be understood, however, that the present invention may be applicable to use in other surgical contexts, such as the removal of tumors in all areas of the human and/or animal body and/or other surgical procedures on humans and/or animals.

Figure 1:
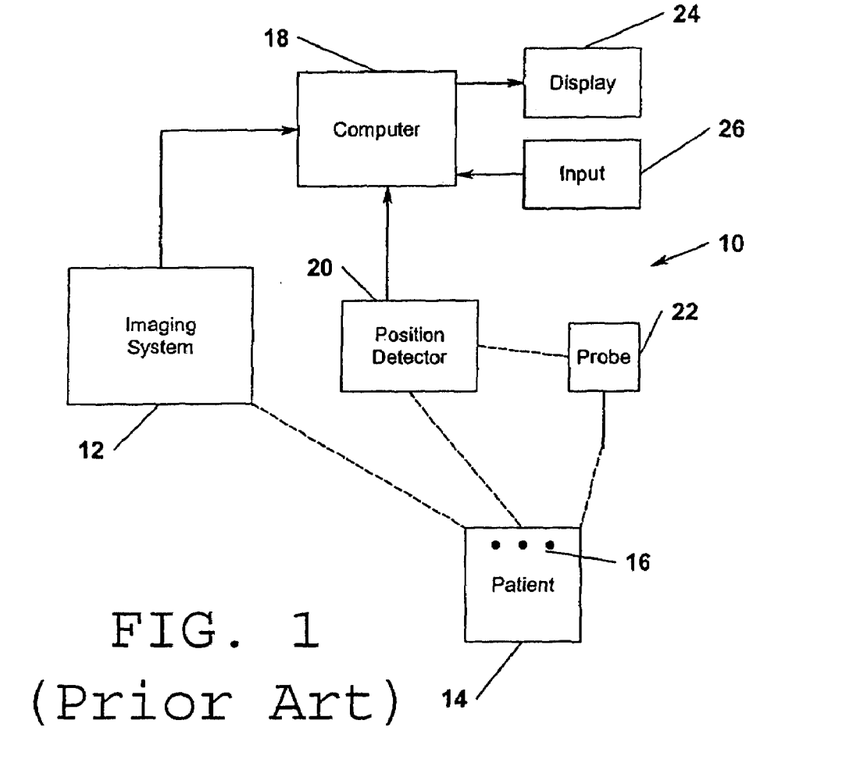
FIG. 1 is a schematic block diagram of an exemplary frameless stereotaxy system with which the present invention may be employed.

The present invention is employed in combination with a conventional frameless stereotaxy system, e.g., as illustrated schematically at 10 in FIG. 1. As described above, a frameless stereotaxy system 10, also known as a neuro-navigation system, allows a surgeon to visualize the position of a probe or other surgical instrument as moved through real three-dimensional space during a surgical procedure with respect to pre-operative images of the area in question. A variety of imaging systems 12 may be used to obtain such pre-operative images of a patient 14. For example, computed tomography (CT), magnetic resonance imaging (MRI), ultrasonagraphic, and/or other imaging systems 12 may be used to obtain multiple two and/or three dimensional images of the patient's internal anatomy. Several markers 16 are placed in fixed positions on the patient's internal or external anatomy before the pre-operative images are obtained. For example, for images obtained of the patient's brain the markers 16 (e.g., 8-12 markers) may be placed around the patient's scalp or in the patient's skull. These markers 16 will remain on the patient during the subsequent surgical procedure that is performed using the frameless stereotaxy system 10 for surgical guidance. The images of these markers 16 appear on the images obtained by the imaging system 12 and, as discussed below, are used to register the pre-operative images obtained with the position of a probe or other medical instrument employed in the frameless stereotaxy system 10. The pre-operative images obtained by the imaging system 12 are provided to a computer system 18 of the frameless stereotaxy system 10. Pre-operative imaging data from the imaging system 12 may be provided to the frameless stereotaxy system computer 18 either via a direct wired or wireless communications link or by physically transporting a computer disk or other conventional physical memory storage medium from the imaging system 12 to the frameless stereotaxy system computer 18.

In a conventional frameless stereotaxy system 10 a position detector system 20 is used to determine the position in real space around and within the patient 14 of a probe 22 or other medical instrument or device. Various different conventional position detection systems 20 are employed in a frameless stereotaxy system 10. For example, an optical system may employ a binocular camera position detector 20 to detect the position of the probe 22 via a plurality of active (e.g., LEDs) or passive markers mounted on the probe 22. Alternatively, an electromagnetic transmitter may be mounted on the probe to produce signals that are detected by an electromagnetic receiver in the position detector 20, thereby to determine the position of the probe 22 in real space. The position of the probe 22 as determined by the position detector 20 is provided to the frameless stereotaxy system computer 18 wherein the probe position information is combined with pre-operative imaging data from the imaging system 12 to provide a computer generated image, e.g., presented on a conventional computer display 24, of the probe position in real space relative to the pre-operative images obtained.

Registration of the real three-dimensional space, in which the probe 22 is moved, with the pre-operative image data may be obtained using the patient markers 16. For example, after the patient is placed in position in the surgical field, the probe 22 may be touched to the patient markers 16 while indicating to the computer 18 which of the markers 16 being touched with the probe corresponds to which markers 16 as appear in the pre-operative images provided to the computer system 18. By detecting the positions of the markers 16 in real space in this manner, the pre-operative image data may be registered to the real-space surgical field. As an alternative to using patient markers 16, registration of the real surgical field to the pre-operative image data may be obtained by correlating the positions of anatomical features of the patient in the surgical field with such features as may appear in the pre-operative images.

A frameless stereotaxy system 10 typically also includes one or more input devices 26, e.g., a keyboard, mouse, and/or track ball, etc. which allows the surgeon to interact with the frameless stereotaxy system computer 18 and the images displayed on the system display 24 thereby, e.g., to select from among a variety of viewing angles or types of images to be displayed. Conventional frameless stereotaxy systems of the type just discussed include the Danek-Stealth system and systems available from BrainLAB AG, and Compass International Incorporated.

An exemplary method 30 in accordance with the present invention, employing marking catheters and a frameless stereotaxy system 10, as described above, to define a brain lesion for removal, will now be described with reference to the flow chart diagram of FIG. 2. The process begins by obtaining 32 pre-operative imaging of the appropriate portion of the patient's body. For example, for the removal of a brain lesion, multiple pre-operative images of the patient's brain may be obtained 32. As discussed above, the pre-operative imaging may include magnetic resonance imaging (MRI), computed tomography (CT) and/or other types of imaging, either alone or in combination. The resulting pre-operative images obtained by the imaging system 12 are stored in the computer system 18. As discussed above, markers 16 may be placed on the patient in the field of view of the pre-operative images such that images of the markers 16 appear in the pre-operative images obtained. Note that pre-operative imaging 32 typically may take place in a separate room from the surgical procedure and before the patient is prepared and positioned for surgery. However, it is also possible that the pre-operative imaging 32 may take place in the operating room after the patient has been prepared and positioned for surgery therein.

After the pre-operative images of the patient have been obtained 32 and the patient is prepared and positioned for surgery it is necessary to register 34 the stereotaxy system, i.e., to register the pre-operative images obtained with the real three-dimensional surgical field in which the operation is to take place. As discussed above, this registration process 34 may be accomplished by indicating the positions in real space of patient markers 16 appearing in the pre-operative images by touching the markers 16 positioned on the patient 14 using the frameless stereotaxy system probe 22. Alternatively, registration 34 of the stereotaxy system to the real surgical field may be accomplished by indicating to the frameless stereotaxy system the locations in real space of anatomical patient features that also appear on the pre-operative images. This may be accomplished using the frameless stereotaxy system probe 22, or another device, such as a laser scanning device which is used to scan the patient's features in the surgical field. The features scanned in this way are provided to the frameless stereotaxy system computer 18 to register the pre-operative images with the patient's features as positioned in the surgical field. An example of this latter type of registration system is the Z-touch markerless registration system available from BrainLab. After registration 34 of the stereotaxy system with the surgical field, the pre-operative images may be employed via the stereotaxy system 10 as an accurate navigational tool for the procedure to follow.

After registration 34 of the stereotaxy system in the manner described above, the surgical site may be prepared 36 in a conventional manner. This may involve, for example, a scalp incision, a craniotomy, etc. For example, for the removal of a brain lesion exposure of the brain in and around the area from which the tumor is to be removed may be required.

In accordance with the present invention, one or more marking catheters are positioned in the patient's body, in this case, in the patient's brain, using a frameless stereotaxy system as a guide, to define a particular area of interest. In the exemplary case being described, one or more marking catheters are positioned in the patient's brain, using the frameless stereotaxy system as a guide, to define the boundaries of a brain lesion that is to be removed.

Figure 3:
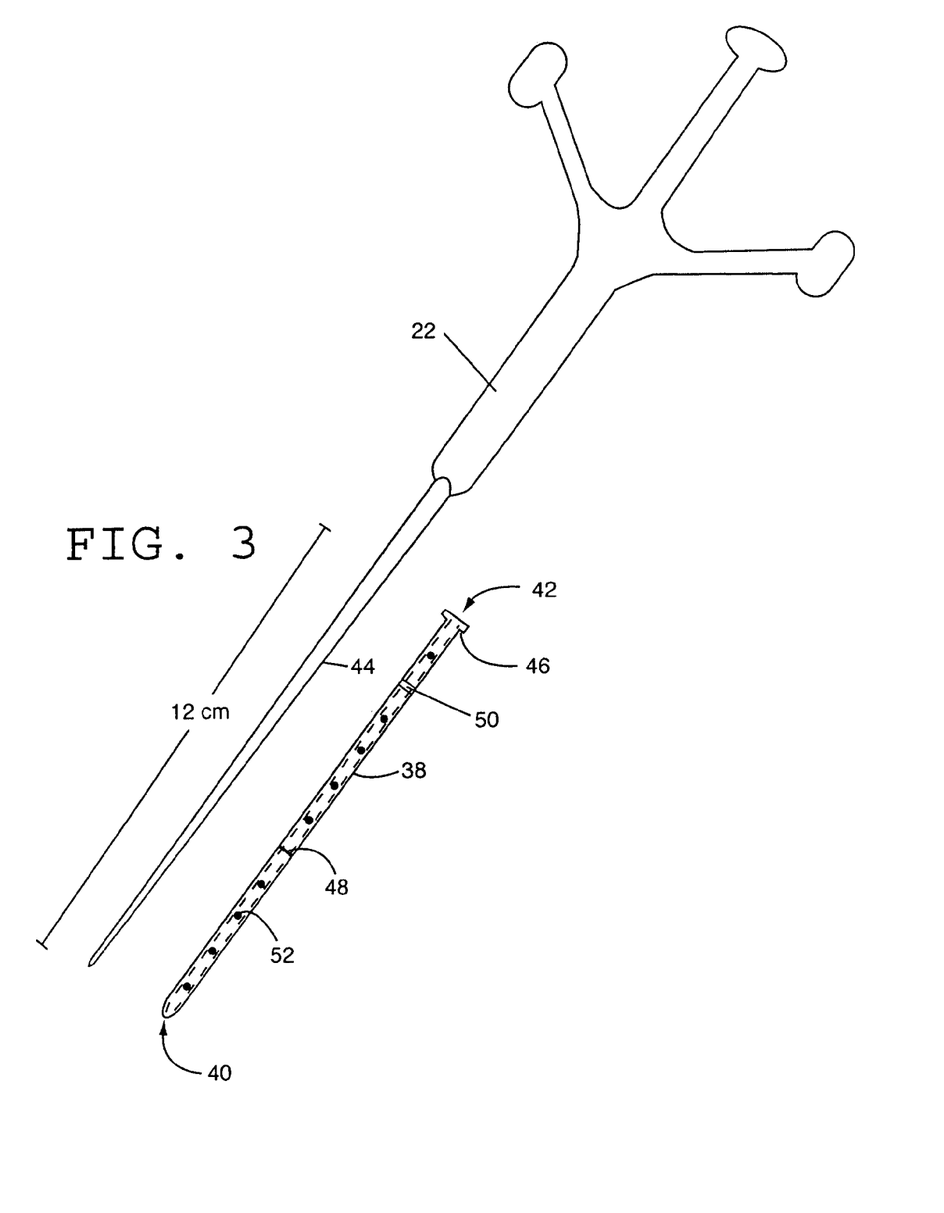
FIG. 3 is an illustration of a marking catheter in accordance with the present invention along with a conventional frameless stereotaxy system probe for use in positioning the marking catheter in the proper position in, e.g., a patient's brain, using a frameless stereotaxy system for guidance.

An exemplary marking catheter 38 in accordance with the present invention is illustrated in FIG. 3. The marking catheter 38 is made of a very soft pliable material, such as silicone rubber (e.g., Silastic), or some other similar material. The marking catheter 38 has a closed distal end 40 and an open proximal end 42. The inner diameter of the catheter 38 is sized such that the catheter is designed to slide over the end 44 of a localizing (navigation) probe 22 of a frameless stereotaxy system, such that the marking catheter 38 remains in place on the tip 44 of the probe 22 as the probe tip 44 is inserted in the brain or other tissue to position the marking catheter 38 therein, and such that the probe 22 is easily removed from the catheter 38, to leave the catheter 38 in the desired position once the catheter 38 has been positioned using the probe 22. Preferably a flange 46 may be provided at or around the open proximal end 42 of the marking catheter 38 to facilitate manually holding the marking catheter 38 in the desired position in the brain or other tissue as the localizing probe 22 is removed therefrom. As will be discussed in more detail below, one or more marking catheters 38 in accordance with the present invention may be used as a visual guide for the complete and effective removal of a brain lesion. Preferably the marking catheter 38 may be made of a brightly colored material, to assist in this visualization.

Length indicators or indicia formed and/or printed so as to be visible on the outer surface of the marking catheter 38 also preferably may be provided to assist the surgeon in visualizing the depth of a target lesion which the marking catheter 38 is used to mark. For example, the marking catheter 38 may be marked off externally with rings, dots, or other length indicators. As illustrated, for exemplary purposes only, the marking catheter 38 may be marked off externally with a single band or ring 48 at five centimeters from the closed distal end 40 of the catheter 38, a double band or ring 50 at 10 centimeters from the closed distal end 40 of the marking catheter 38, and dots 52 at one centimeter incremental lengths between the distal end 40 of the marking catheter 38 and the ring length indications 48 and 50. It should be noted that various other and/or different length indicating marks or indicia may be used in accordance with the present invention. It should also be noted that marking catheters 38 in accordance with the present invention may be of any useful length and may be adapted to be used with any or a variety of frameless stereotaxy system probes 22, and are not limited to the specific length or for use with the specific probe 22 illustrated, for example, in FIG. 3.

A marking catheter 38 in accordance with the present invention is preferably a one-time-use only disposable product. However, a marking catheter 38 in accordance with the present invention may also or alternatively be made of a flexible material that can be sterilized and reused.

Figure 2:
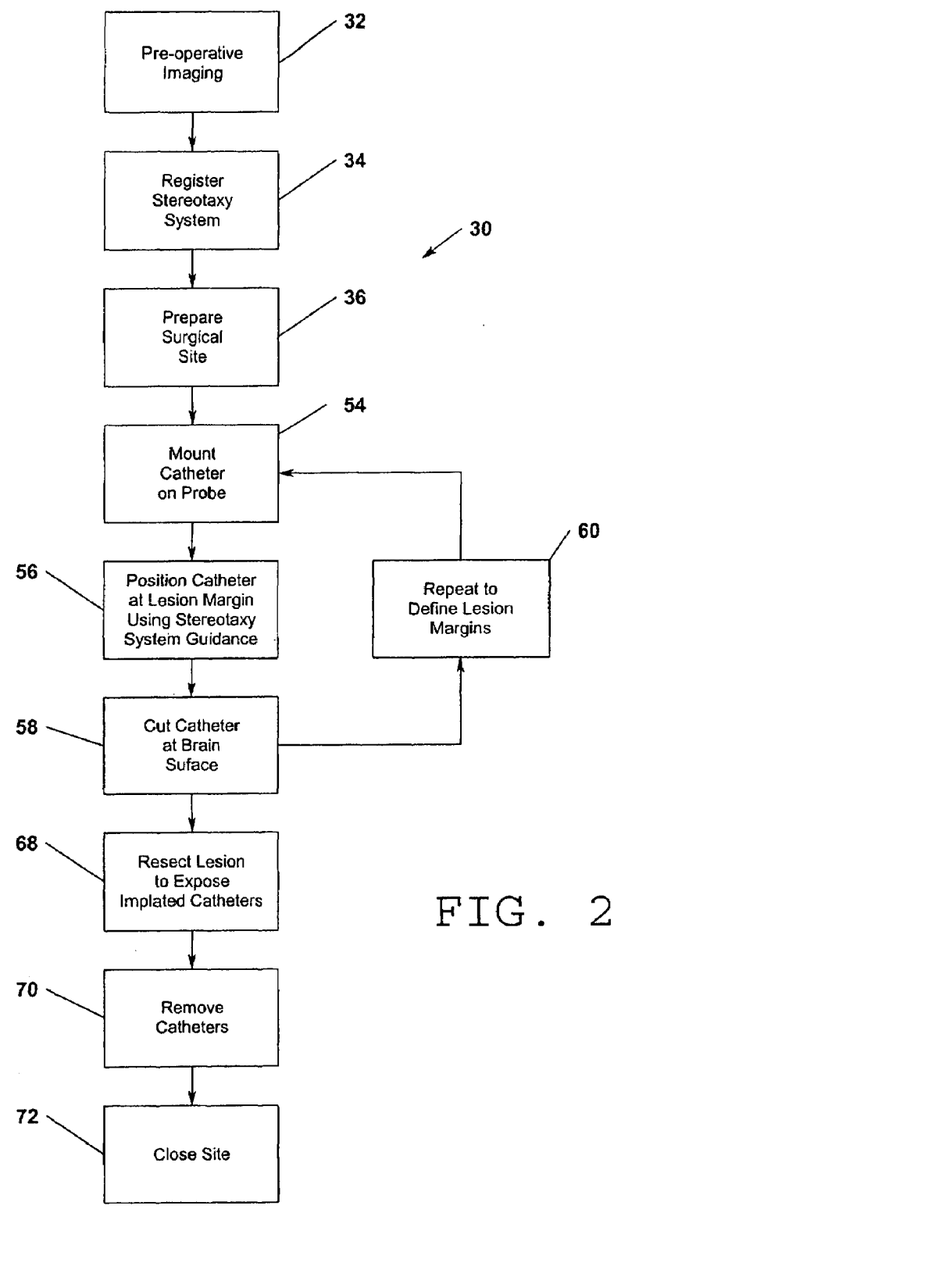
FIG. 2 is a flow chart diagram illustrating the exemplary steps of a procedure for resecting a brain lesion employing the present invention.

Returning now to the discussion of the exemplary procedure for employing one or more marking catheters 38 in accordance with the present invention as illustrated in FIG. 2. After the surgical site has been prepared 36 a marking catheter 38 in accordance with the present invention is mounted 54 on the tip of the frameless stereotaxy system probe 22. Using the frameless stereotaxy system 10 for guidance, the probe 22 is then used to position 56 the marking catheter 38 in a position physically to mark a desired area. For example, the frameless stereotaxy system probe 22 may be used to position 56 the marking catheter 38 in a patient's brain along the margin of a brain lesion to be removed, with the closed distal end 40 of the marking catheter 38 extended to the lesion depth.

Once the marking catheter 38 in accordance with the present invention is placed 56 in the desired position, using the frameless stereotaxy system 10 for guidance, the frameless stereotaxy system probe 22 may be removed from the catheter 38, e.g., by pulling back on the probe 22 as the marking catheter 38 is physically held in position, e.g., at the flanged 46 proximal end 42 thereof. Once the frameless stereotaxy system probe 22 is removed from the catheter 38, the flexible catheter 38 may be cut off 58 at or near the surface of the brain.

Figure 4:
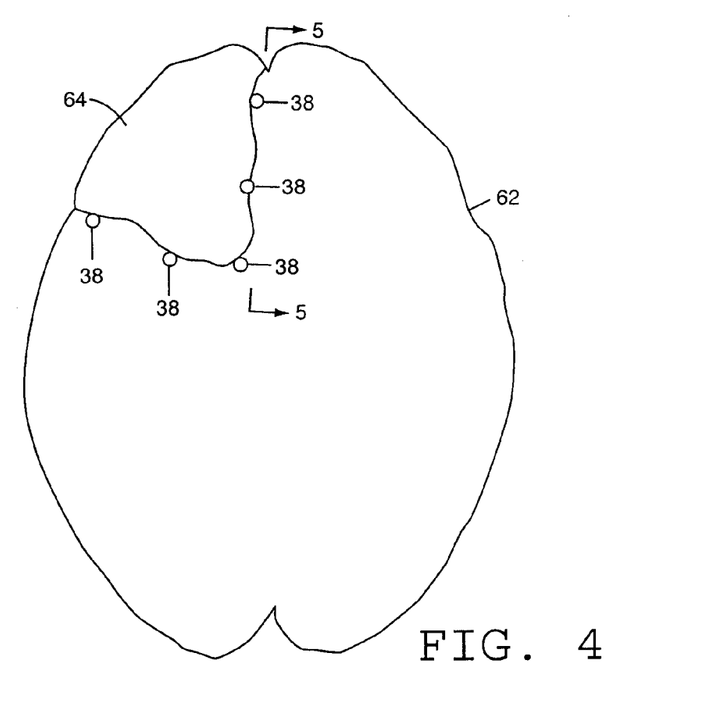
FIG. 4 is a schematic top view of a human brain showing the exemplary positioning of marking catheters in accordance with the present invention around a brain lesion to define the margins thereof.
Figure 5:
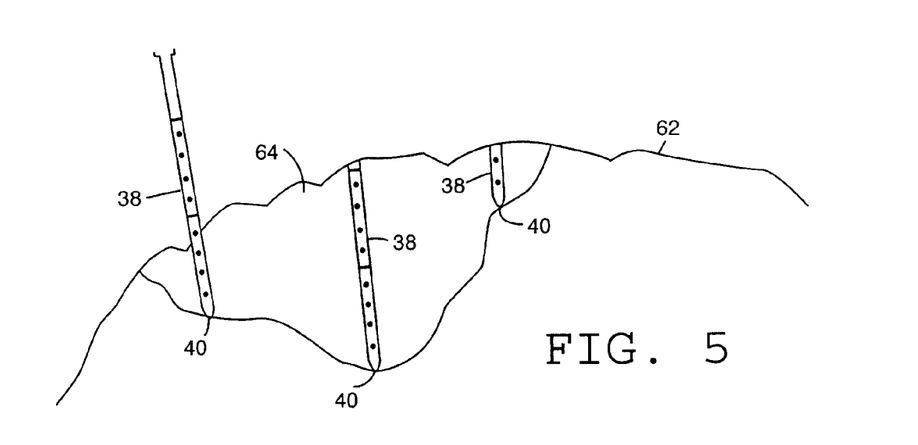
FIG. 5 is a schematic cross-section view of a portion of the brain illustrated in FIG. 4.

The process of mounting 54 a marking catheter 38 on a frameless stereotaxy system probe 22, positioning 56 the marker 38 in the brain using the probe 22, and cutting off 58 the positioned marking catheter 38 at the brain's surface may be repeated 60 as necessary, e.g., to define the margins of a brain lesion. Thus, for example, as illustrated in a very simplified manner in FIGS. 4 and 5, a plurality of marking catheters 38 in accordance with the present invention may be positioned in the brain 62 using the frameless stereotaxy system 10 as a guide, in the manner just described, to define the margins of a brain lesion 64, i.e., the border between the lesion 64 and normal brain tissue. As illustrated in FIG. 5, the one or more marking catheters 38 preferably are extended into the brain tissue to the appropriate depth such that the distal ends 40 of the marking catheters 38 are positioned at the margin of the lesion 64, between the lesion 64 and normal brain tissue. (Note that FIG. 5 shows two of the marking catheters 38 positioned in the brain cut off at the brain surface and one marking catheter that has not yet been cut off.) Thus, the one or more marking catheters 38 in accordance with the present invention provide a visual boundary in the surgical field of the lesion 64 to be removed. Note that for a very small lesion it may be desired to use a single marking catheter 38 in accordance with the present invention positioned through the center or near center of the lesion to the appropriate depth, using the frameless stereotaxy system 10 for guidance, to indicate the lesion depth alone, rather than the entire margin of the lesion.

After the one or more marking catheters 38 in accordance with the present invention have been positioned as desired to define the margins of a brain lesion 64, resection 68 of the lesion may proceed in a conventional manner. For example, a conventional ultrasonic aspirator or other device may be used to remove 68 the lesion 64. As the lesion 64 is removed 68 the implanted marking catheters 38 are exposed. Since the marking catheters 38 were positioned using the frameless stereotaxy system 10 to define the lesion margins, once all of the marking catheters 38 are exposed along their entire length the marked lesion 64 is entirely removed.

As the lesion is removed 68 the brain 62 may shift position. As discussed above, this may result from a variety of phenomena, including the movement of normal brain material into the area from which the lesion is being removed. However, since the marking catheters 38 are made of a very flexible material, the marking catheters 38 positioned in the brain 62 will move along with the shifting brain, thus maintaining their positions in the brain 62 at the margin between the lesion 64 and normal brain. As discussed above, if brain-shift occurs, a frameless stereotaxy system 10 cannot be relied upon for navigation in the brain, because the frameless stereotaxy system 10 relies on pre-operative images of the brain. With the use of marking catheters 38 in accordance with the present invention, however, a brain lesion can accurately and completely be removed since the frameless stereotaxy system is used accurately to physically define the lesion margins using the marking catheters 38 before any brain-shift resulting from lesion removal actually occurs. Thus, the present invention takes advantage of the accuracy of frameless stereotaxy systems as a means for neuro-navigation before brain-shift occurs, in a simplified manner that allows the accurate definition of the lesion margin in a manner that maintains its accuracy after brain-shift occurs without requiring intraoperative imaging or any other complicated, expensive, or unreliable means for correcting the frameless stereotaxy system to compensate for brain-shift occurring during surgery.

After the brain lesion 64 has been removed 68 the marking catheters 38 may be removed 70 from the brain in a conventional manner, and disposed of. The surgical site may then be closed 72 and the patient transitioned to recovery.

The present invention was used, for example, for the removal of a large irregular six to seven centimeter tumor involving the right frontal lobe of a 64 year old gentleman presenting with cognitive difficulties. The patient was prepared for surgery utilizing the Stealth system for frameless interactive intra-operative guidance. At surgery, a very large, partially necrotic tumor was identified, extending out to the surface of the brain. Visually, the tumor blended imperceptibly with normal brain tissue, making gross total tumor resection difficult by conventional methods. Prior to tumor removal, the Stealth frameless stereotaxy system was used to place four small Silastic marking catheters in accordance with the present invention to outline the posterior and medial margins of the tumor. The catheters were inserted to define the maximum depth of the tumor at the four locations and then cut off flush with the surface of the brain. The tumor was then resected using conventional micro-surgical techniques. Tumor removal continued until the catheters were exposed down to their tips, marking the maximum depth as well as the perimeter of the tumor as seen on pre-operative MRI and CT scans. Since the catheters are soft and pliable, they moved as the surrounding brain shifted into the cavity of tumor resection, virtually eliminating the error associated with brain-shift. Once all four catheters were exposed by way of tumor resection, the surgeon was assured that gross total tumor removal had been accomplished. Post-operatively, the patient has done very well without any additional neurological deficits in spite of resection of a tumor approximately the size of a large orange. A post-operative MRI scan performed one day after surgery confirmed complete tumor removal. Considering the large, irregular shape of the tumor pre-operatively, the post-operative result is excellent. As this tumor was determined to be a malignant glioma, and several studies point to a strong correlation between the extent of initial tumor resection and long-term quality of life survival, the importance of the present invention in aiding the surgeon to achieve improved results for this patient cannot be over emphasized. This technique has also been found to be extremely useful in tumors of all sizes involving the brain perenchyma, especially those causing distortion of normal anatomy.

It should be understood that the present invention is not limited to the particular exemplary applications and embodiments illustrated and described herein, but embraces all modified forms thereof that come within the scope of the following claims. It should be understood that the term lesion as used throughout this application, including in the claims, refers generically to any impaired area, including any type of tumor.

What is claimed is:

1. A flexible marking catheter system for placement in a selected position in a body using a frameless stereotaxy system, comprising:
   a frameless stereotaxy system probe; and
   a flexible catheter body made of a flexible material and having a closed distal end and an open proximal end and sized to removably fit on the frameless stereotaxy system probe and mounted on the frameless stereotaxy system probe such that the catheter remains on the probe as the catheter is positioned in a body using the probe and such that the probe is removable from the catheter without moving the catheter after the catheter is positioned in the body using the probe.

2. The flexible marking catheter system of claim 1 wherein the catheter body is made of silicone rubber.

3. The flexible marking catheter system of claim 1 comprising additionally a flange at the open proximal end of the flexible catheter body to facilitate removing the probe from the catheter after the catheter is positioned in the body using the probe.

4. The flexible marking catheter system of claim 1 comprising additionally length indicia visible on an outer surface of the flexible catheter body indicating distances along the catheter body from the distal end thereof.

5. The flexible marking catheter system of claim 4 wherein the length indicia indicate centimeter distances along the catheter body from the distal end thereof.

6. The flexible marking catheter system of claim 5 wherein the length indicia include rings visible around an outer surface of the flexible catheter body at five centimeters from the distal end thereof and at ten centimeters from the distal end thereof and dots visible on the outer surface of the flexible catheter body at one, two, three, four, six, seven, eight, and nine centimeters from the distal end thereof.

7. The flexible marking catheter system of claim 6 wherein the length indicia includes a double ring visible around the outer surface of the flexible catheter body at ten centimeters from the distal end thereof.

8. The flexible marking catheter system of claim 1 wherein the flexible catheter body is made of a brightly colored material.

9. A flexible marking catheter system for placement in a selected position in a body using a frameless stereotaxy system, comprising:
   a frameless stereotaxy system probe;
   a flexible catheter body made of a flexible material and having a closed distal end and an open proximal end and sized to removably fit on the frameless stereotaxy system probe and mounted on the frameless stereotaxy system probe such that the catheter remains on the probe as the catheter is positioned in the body using the probe and such that the probe is removable from the catheter without moving the catheter after the catheter is positioned in the body using the probe;
   a flange at the open proximal end of the flexible catheter body to facilitate removing the probe from the catheter after the catheter is positioned in the body using the probe; and length indicia visible on an outer surface of the flexible catheter body indicating distances along the catheter body from the distal end thereof.

10. The flexible marking catheter system of claim 9 wherein the catheter body is made of silicone rubber.

11. The flexible marking catheter system of claim 9 wherein the length indicia indicate centimeter distances along the catheter body from the distal end thereof.

12. The flexible marking catheter system of claim 11 wherein the length indicia include rings visible around an outer surface of the flexible catheter body at five centimeters from the distal end thereof and at ten centimeters from the distal end thereof and dots visible on the outer surface of the flexible catheter body at one, two, three, four, six, seven, eight, and nine centimeters from the distal end thereof.

13. The flexible marking catheter system of claim 12 wherein the length indicia includes a double ring visible around the outer surface of the flexible catheter body at ten centimeters from the distal end thereof.

14. The flexible marking catheter system of claim 9 wherein the flexible catheter body is made of a brightly colored material.

* * * * *